United States Patent [19]

Donaldson

[11] Patent Number: 4,549,539
[45] Date of Patent: Oct. 29, 1985

[54] METHOD FOR PROTECTION OF THE EYE

[76] Inventor: William B. M. Donaldson, 45 Carlton Pl., Aberdeen, AB2 4BR, Scotland

[21] Appl. No.: 507,106

[22] Filed: Jun. 23, 1983

[30] Foreign Application Priority Data

Jul. 3, 1982 [GB] United Kingdom ................. 8219300

[51] Int. Cl.[4] ............................................ A61F 13/00
[52] U.S. Cl. .................... 128/132 R; 604/294
[58] Field of Search ....................... 604/294, 302, 303; 2/15; 128/76.5, 128, 335, 163, 155, 156, 132 R

[56] References Cited

U.S. PATENT DOCUMENTS

| | | | |
|---|---|---|---|
| 2,303,131 | 11/1942 | Morgan | 128/156 X |
| 3,516,409 | 6/1970 | Howell | 128/335 |
| 3,926,193 | 12/1975 | Hasson | 128/335 |
| 3,933,158 | 1/1976 | Haverstock | 128/335 |
| 3,983,878 | 10/1976 | Kawchitch | 128/335 |
| 4,038,989 | 8/1977 | Sierra et al. | 128/335 |
| 4,134,401 | 1/1979 | Galician | |
| 4,411,263 | 10/1983 | Cook | 128/132 |

Primary Examiner—C. Fred Rosenbaum
Assistant Examiner—Christa K. Scott
Attorney, Agent, or Firm—Arnold, White & Durkee

[57] ABSTRACT

A surgical appliance for use in procedures for treating the eye consists of two adhesive strips one for attachment to the eye upper lid and the other for attachment to the cheek below the eye. The strips are interconnected by a releasable stud-and-tab fastener, not adversely affected by fluid discharge or treatment solutions, operable repeatedly to reclose the eye with the same tension and positioning of the eyelid on each occasion.

2 Claims, 5 Drawing Figures

METHOD FOR PROTECTION OF THE EYE

This invention relates to a medical or surgical appliance for use in procedures for treating the eye and to a method of closure of the eye between treatments.

The invention is concerned particularly with the protection of the eye.

A conventional method of protecting the eye and keeping the same closed between treatments is to use a pad made of cotton wool sandwiched between layers of gauze. The pad is placed over the eye and held in position by adhesive tape or bandage. This conventional method has the disadvantages that the position of the eyelid under the pad is unknown and the eye may be able to open with resultant abrasion of the cornea directly from the eye pad; it is impossible to know how much pressure is being applied to the eye; the pressure of the eyepad can cause the eyelashes to turn inwards and abrase the globe; the pressure of an eyepad can disrupt the normal flow of tears under the eyelid; the pressure of an eyepad may also prevent the escape of pus from under the eyelids; and eyepads are usually supplied several in each sterile packet and the sterility of the remaining pads must be lost when the packet is opened and the first eyepad is removed for use.

An object of the present invention is to provide an appliance for use in procedures for treating the eye whereby the said disadvantages may be obviated or mitigated.

According to one aspect of the present invention, there is provided an appliance for use in procedures for treating the eye, comprising first and second elements for attachment respectively to an eye upper lid and to a part of the cheek below the eye, and repeatedly openable and reclosable fastening means interconnecting said elements to enable repeated ready access to the eye and repeated reclosure thereof.

In use, the first and second elements are attached respectively to the eye upper lid and to the cheek below the eye, and the fastening means fastened to interconnect the elements so to hold the eyelid closed. The eyelid is the ideal eye protector, its function being unimpaired by the first element. The releasable fastening means allows ready and repeated access to the eye.

Thus, according to another aspect of the present invention, in treatment of the eye, closure thereof between exposure of the eyeball for examination and treatment is effected by fastening means interconnecting first and second elements, one of which is attached to the upper eye lid and the other of which is attached to a part of the cheek below the eye, the fastening means being adapted for repeated opening and reclosing to enable repeated ready access to the eye and repeated reclosure thereof.

An embodiment of the present invention will now be described, by way of example, with reference to the accompanying drawings in which.

Figures 1, 2:
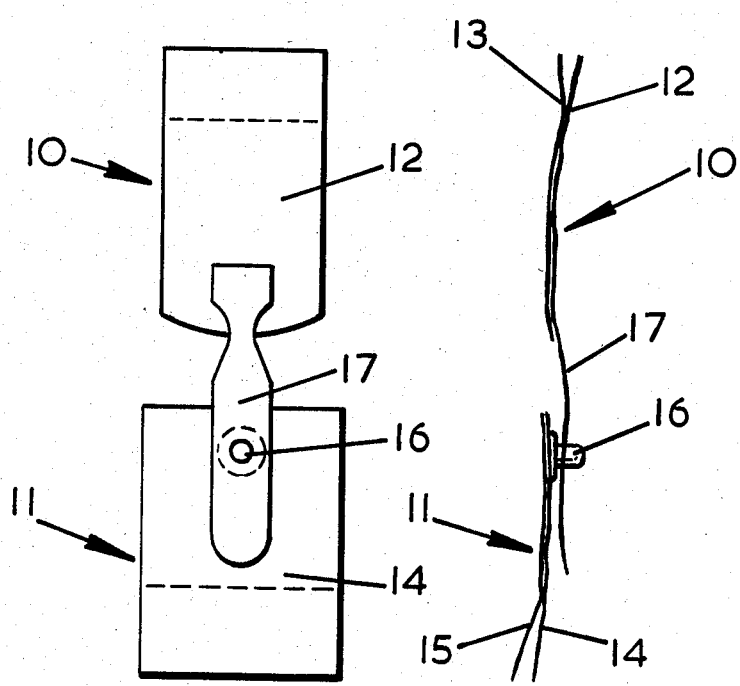
FIG. 1 is a diagramatic front elevation of an appliance in accordance with the present invention.
FIG. 2 is a side elevation of the appliance of FIG. 1.

In the drawings, with reference first to FIGS. 1 and 2, the appliance consists of first and second elements respectively indicated by reference numerals 10 and 11.

The element 10 consists of a strip 12 of a flexible plastics material and having an adhesive coating on one side which is covered by a pull-off protective layer or 'backing' 13. The adhesive stops short of the upper portion of the strip 12 for ease of handling, and removal of the protective layer 13. Similarly, the element 11 consists of a strip 14 of a flexible plastics material having an adhesive coating and a removable 'backing' 15. The elements 10 and 11 are interconnected by releasable fastening means in the form of a stud 16 and tab 17. The stud 16 is fixed to the surface of the strip 14. The tab 17 has its upper end fixed to the lower portion of the strip 12, and has an aperture for engagement over the stud 16. The tab is also made of flexible plastics material. The lower edge portion of the strip 12 is shaped generally to the contour of the eyelid. The strips 12 and 14 are preferably of a colourless translucent material, or they may be coloured to match flesh tones; and these strips may be perforated or porous in the interests of maintaining a good condition of the skin beneath the strips when in use.

Figure 3:
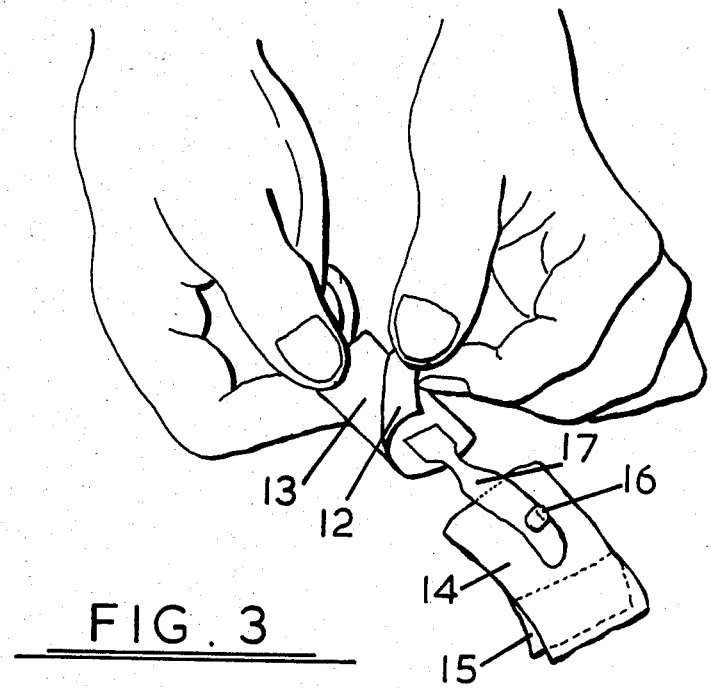
FIG. 3 shows a perspective view (to a smaller scale than FIGS. 1 and 2) of the appliance being prepared for use.
Figure 4:
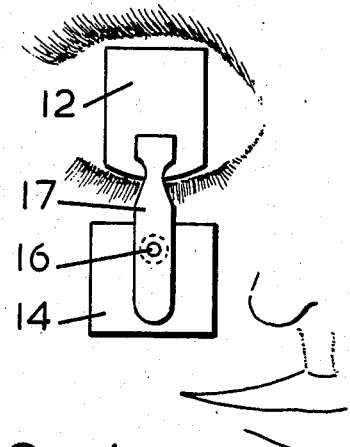
FIG. 4 shows the appliance in use to hold an eyelid closed.

In preparing the appliance for use, the 'backing' strip 13 is removed from the first element 10 as shown in FIG. 3. Then, with the patient's eye closed and looking downwards, the element 10 is applied to the cleaned upper eyelid from just above the lash line upwards. Next, the backing is removed from the second element 11 and the latter is positioned on the cheek below the eye to hold the upper lid in a satisfactorily closed position with just the correct tension to keep the eye closed without excessively dragging the upper lid downwards. Thereafter, the non-adhesive portions of the strips 12 and 14 may be trimmed away to leave the appliance in use as is shown in FIG. 4.

Figure 5:
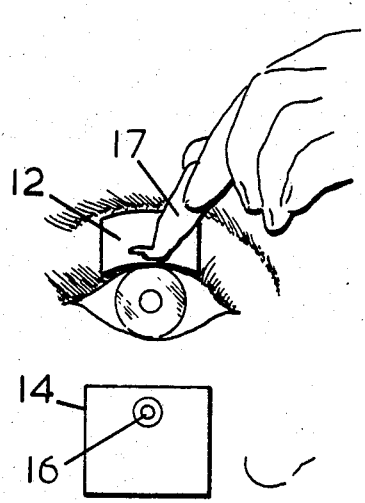
FIG. 5 shows the appliance in use giving temporary access to the eye.

When access to the eye is required, for example to instill drops (see FIG. 5), the tab 17 is pulled off the stud 16 and lifted up to open the eye. In order to reclose the eye, the tab 17 is simply re-engaged with the stud 16, thereby closing the eye with the same tension and positioning as obtained on first application of the appliance.

Modifications of the appliance described above, within the scope of the present invention, include using virtually any suitable releasable fastening means for interconnecting the first and second elements. The preferred form of fastening means is adapted so that repeated use of the fastening means recloses the eye with the same tension and positioning of the eyelid on each occasion. For example, an eye and hook fastening means may be used in place of the tab and stud. A touch-and-close fastening means such as that available under the Trade Mark VELCRO may be used with equal effect. The preferred form of fastening means is not significantly adversely affected by fluid discharge from the eye, nor by treatment solutions. It is envisaged that means other than adhesive may be used to attach the elements. For example, the elements may be attached by sutures.

I claim:

1. A method for treatment of the eye, closure thereof between exposures of the eyeball for examination and treatment is effected by fastening means interconnecting first and second elements one of which is attached to the upper eyelid and the other of which is attached to a part of the cheek below the eye, the fastening means being adapted for repeated opening and reclosing to enable repeated ready access to the eye and repeated reclosure thereof.

2. A method for treatment of the eye as claimed in claim 1, the first and/or the second element comprises an adhesive strip.

* * * * *